(12) United States Patent
Zipprich

(10) Patent No.: US 9,393,086 B2
(45) Date of Patent: Jul. 19, 2016

(54) DENTAL IMPLANT SYSTEM

(76) Inventor: Holger Zipprich, Malchen (DE)

( * ) Notice: Subject to any disclaimer, the term of this patent is extended or adjusted under 35 U.S.C. 154(b) by 0 days.

(21) Appl. No.: 13/982,799

(22) PCT Filed: Jan. 31, 2012

(86) PCT No.: PCT/EP2012/000413
§ 371 (c)(1),
(2), (4) Date: Oct. 14, 2013

(87) PCT Pub. No.: WO2012/104061
PCT Pub. Date: Aug. 9, 2012

(65) Prior Publication Data
US 2014/0212844 A1  Jul. 31, 2014

(30) Foreign Application Priority Data
Jan. 31, 2011  (DE) .......................... 10 2011 009 906

(51) Int. Cl.
*A61C 8/00* (2006.01)

(52) U.S. Cl.
CPC .............. *A61C 8/0022* (2013.01); *A61C 8/005* (2013.01); *A61C 8/006* (2013.01); *A61C 8/0068* (2013.01); *A61C 8/0069* (2013.01)

(58) Field of Classification Search
CPC .................................................... A61C 8/0022
USPC .................................................. 433/172–176
See application file for complete search history.

(56) References Cited

U.S. PATENT DOCUMENTS

| 4,270,905 A | 6/1981 | Mohammed |
| 4,324,550 A | 4/1982 | Reuther et al. |
| 4,731,085 A | 3/1988 | Koch |

(Continued)

FOREIGN PATENT DOCUMENTS

| CH | 642838 | 5/1984 |
| CH | 696625 | 8/2007 |

(Continued)

OTHER PUBLICATIONS

International Search Report prepared by the European Patent Office on Jul. 31, 2007, for International Application No. PCT/EP2007/003480; Applicant, Holger Zipprich.

(Continued)

*Primary Examiner* — Ralph Lewis
(74) *Attorney, Agent, or Firm* — Sheridan Ross P.C.

(57) ABSTRACT

A dental-implant system having a first implant part provided for being inserted into a jawbone and having a second implant part associated therewith, provided for fixing a dental prosthetic piece, the implant parts being mechanically connectable to each other via a connection pin which is formed onto one of the implant parts and which can be pushed into a receiving channel provided in the other implant part, and the cross-section of the connection pin and the cross-section of the receiving channel associated therewith each presenting in an indexing area a number of main directions in which the radius takes in each case a relative maximum value, shall offer an even increased mechanic load-carrying ability and thus a particularly long service life when used in the patient's mouth. For this purpose, according to the invention, the outer cross-section of the implant part including the receiving channel is configured such that its radius also takes a relative maximum value within a tolerance range of each of the main directions.

20 Claims, 5 Drawing Sheets

(56) References Cited

U.S. PATENT DOCUMENTS

| | | | |
|---|---|---|---|
| 4,793,808 A | 12/1988 | Kirsch | |
| 4,832,601 A | 5/1989 | Linden | |
| 4,850,870 A | 7/1989 | Lazzara et al. | |
| 4,854,872 A | 8/1989 | Detsch | |
| 4,876,148 A | 10/1989 | Virkar | |
| 5,015,186 A | 5/1991 | Detsch | |
| 5,125,971 A | 6/1992 | Nonami et al. | |
| 5,135,395 A | 8/1992 | Marlin | |
| 5,195,892 A | 3/1993 | Gersberg | |
| 5,246,370 A * | 9/1993 | Coatoam | 433/173 |
| 5,281,140 A | 1/1994 | Niznick | |
| 5,302,126 A | 4/1994 | Wimmer et al. | |
| 5,336,465 A | 8/1994 | Matsunaga et al. | |
| 5,407,359 A | 4/1995 | Balfour et al. | |
| 5,425,639 A | 6/1995 | Anders | |
| 5,437,551 A | 8/1995 | Chalifoux | |
| 5,553,983 A | 9/1996 | Shinjo | |
| 5,674,072 A | 10/1997 | Moser et al. | |
| 5,766,179 A | 6/1998 | Faccioli et al. | |
| 5,782,918 A | 7/1998 | Klardie et al. | |
| 5,785,525 A * | 7/1998 | Weissman | 433/174 |
| 5,947,733 A | 9/1999 | Sutter et al. | |
| 5,954,505 A | 9/1999 | Ford | |
| 5,984,680 A | 11/1999 | Rogers | |
| 5,989,026 A | 11/1999 | Rogers et al. | |
| 6,158,310 A | 12/2000 | Goss et al. | |
| 6,217,331 B1 | 4/2001 | Rogers et al. | |
| 6,419,489 B1 | 7/2002 | Jorneus et al. | |
| 6,500,003 B2 | 12/2002 | Nichinonni | |
| 6,537,069 B1 * | 3/2003 | Simmons, Jr. | 433/173 |
| 6,575,057 B1 | 6/2003 | Ploeger | |
| 6,652,765 B1 | 11/2003 | Beaty | |
| 7,144,622 B1 | 12/2006 | Stecher et al. | |
| 7,225,710 B2 | 6/2007 | Pacheco, Jr. | |
| 7,249,949 B2 | 7/2007 | Carter | |
| 7,309,231 B2 | 12/2007 | Engman | |
| 8,123,524 B2 | 2/2012 | Anitua | |
| 8,291,795 B2 | 10/2012 | Hughes et al. | |
| 8,347,761 B2 | 1/2013 | Goss | |
| 8,932,663 B2 | 1/2015 | Ritz et al. | |
| 2002/0177105 A1 | 11/2002 | Engman | |
| 2003/0013068 A1 | 1/2003 | Gittleman | |
| 2003/0194679 A1 | 10/2003 | Odrich et al. | |
| 2004/0121285 A1 | 6/2004 | Wu | |
| 2004/0185417 A1 | 9/2004 | Rassoli | |
| 2004/0185419 A1 | 9/2004 | Schulter et al. | |
| 2005/0042573 A1 | 2/2005 | Lustig et al. | |
| 2005/0166724 A1 | 8/2005 | Castaneda | |
| 2005/0186537 A1 | 8/2005 | Gersberg | |
| 2006/0110706 A1 | 5/2006 | Jorneus et al. | |
| 2006/0141418 A1 | 6/2006 | Heo | |
| 2006/0172257 A1 | 8/2006 | Niznick | |
| 2007/0037121 A1 | 2/2007 | Carter | |
| 2008/0182227 A1 | 7/2008 | Wolf et al. | |
| 2008/0241789 A1 | 10/2008 | Mundorf | |
| 2008/0241792 A1 | 10/2008 | Rossler et al. | |
| 2008/0261176 A1 | 10/2008 | Hurson | |
| 2008/0261178 A1 | 10/2008 | Homann et al. | |
| 2008/0293015 A1 | 11/2008 | Wong et al. | |
| 2009/0075236 A1 | 3/2009 | Towse et al. | |
| 2009/0123889 A1 | 5/2009 | Mehrhof | |
| 2009/0123890 A1 | 5/2009 | Purga et al. | |
| 2009/0123891 A1 | 5/2009 | Rosenberg et al. | |
| 2009/0239195 A1 | 9/2009 | Wohrle et al. | |
| 2009/0305190 A1 | 12/2009 | Zipprich | |
| 2010/0099058 A1 | 4/2010 | Wang et al. | |
| 2010/0178636 A1 | 7/2010 | Stephan et al. | |
| 2010/0196851 A1 | 8/2010 | Konig | |
| 2010/0196852 A1 | 8/2010 | Baruc et al. | |
| 2010/0240009 A1 * | 9/2010 | Gogarnoiu | 433/173 |
| 2010/0304334 A1 | 12/2010 | Layton | |
| 2011/0065064 A1 | 3/2011 | Kahdemann et al. | |
| 2011/0123951 A1 | 5/2011 | Lomicka et al. | |
| 2011/0223562 A1 | 9/2011 | Zipprich | |
| 2012/0288824 A1 | 11/2012 | Nordin et al. | |
| 2013/0108984 A1 | 5/2013 | Zipprich | |
| 2013/0337410 A1 * | 12/2013 | Ten Bruggenkate | 433/174 |
| 2014/0106305 A1 * | 4/2014 | Jacoby et al. | 433/174 |
| 2014/0134570 A1 | 5/2014 | Zipprich et al. | |
| 2015/0037759 A1 | 2/2015 | Zipprich | |
| 2015/0157427 A1 | 6/2015 | Purga et al. | |

FOREIGN PATENT DOCUMENTS

| | | |
|---|---|---|
| CN | 2216818 | 1/1996 |
| CN | 1889896 | 1/2007 |
| CN | 101188982 | 5/2008 |
| CN | 101252891 | 8/2008 |
| CN | 101878003 | 11/2010 |
| CN | 102202598 | 9/2011 |
| DE | 19959366 | 6/2001 |
| DE | 10340059 | 2/2005 |
| DE | 69636845 | 8/2007 |
| DE | 10 2006 036020 A1 | 2/2008 |
| DE | 10 2008 05438 A1 | 5/2010 |
| DE | 102008054138 | 5/2010 |
| EP | 0015599 | 9/1980 |
| EP | 1062916 | 12/2000 |
| EP | 1547543 | 6/2005 |
| EP | 2039320 | 3/2009 |
| KR | 10-2007-0009060 | 1/2007 |
| WO | WO 97/43977 | 11/1997 |
| WO | WO 99/62466 | 10/1999 |
| WO | WO 02/26154 | 4/2002 |
| WO | WO 2004/008983 | 1/2004 |
| WO | WO 2004/073541 A2 | 9/2004 |
| WO | WO 2004/080328 | 9/2004 |
| WO | WO 2006/109176 A1 | 10/2006 |
| WO | WO 2008/011948 | 1/2008 |
| WO | WO 2010/049135 | 5/2010 |

OTHER PUBLICATIONS

Written Opinion for International (PCT) Application No. PCT/EP2007/003480, mailed Apr. 20, 2007.
International Preliminary Report on Patentability prepared by the International Preliminary Examining Authority for International Application No. PCT/EP2007/003480 and English translation.
International Search Report prepared by the European Patent Office on Aug. 18 2011 for International Application No. PCT/EP2011/002229.
International Search Report and Written Opinion prepared by the European Patent Office on Mar. 14, 2012, for International Application No. PCT/EP2011/005748.
Official Action for U.S. Appl. No. 12/297,570 mailed Apr. 11, 2011, 15 pages.
Official Action for U.S. Appl. No. 12/297,570 mailed Jan. 5, 2012, 9 pages.
Official Action for U.S. Appl. No. 12/297,570 mailed Jan. 3, 2013, 18 pages.
Official Action for U.S. Appl. No. 12/297,570 mailed May 31, 2013, 18 pages.
Official Action for U.S. Appl. No. 13/696,162 mailed Apr. 12, 2013, 15 pages.
Official Action for U.S. Appl. No. 13/696,162 mailed Feb. 24, 2014, 15 pages.
International Search Report prepared by the European Patent Office on May 14, 2012, for International Application No. PCT/EP2012/000413.
Official Action for German Patent Application No. 102006018726.1, dated Jun. 24, 2015, 6 pages.
Official Action with English Translation for China Patent Application No. 201180062921.5, dated May 13, 2015, 13 pages.
Official Action with English Translation for China Patent Application No. 201280010689.5, dated Jul. 20, 2015, 11 pages.
International Search Report prepared by the European Patent Office on Jul. 30, 2012, for International Application No. PCT/EP2012/001220.
Official Action with English Translation for China Patent Application No. 201280012017.8, dated Jun. 23, 2015, 12 pages.

(56) References Cited

OTHER PUBLICATIONS

Office Action for U.S. Appl. No. 14/003,917, mailed Jun. 30, 2014 8 pages.

Official Action for U.S. Appl. No. 14/003,917, mailed Jan. 15, 2015 8 pages.

Official Action for U.S. Appl. No. 13/696,162, mailed May 6, 2015 12 pages.

Official Action for U.S. Appl. No. 13/885,643, mailed Apr. 9, 2015 18 pages.

Official Action for U.S. Appl. No. 13/696,162 mailed Jul. 18, 2014, 20 pages.

* cited by examiner

DENTAL IMPLANT SYSTEM

CROSS REFERENCE TO RELATED APPLICATIONS

This application is a national stage application under 35 U.S.C. 371 and claims the benefit of PCT Application No. PCT/EP2012/000413 having an international filing date of 31 Jan. 2012, which designated the United States, and which PCT application claimed the benefit of German Patent Application No. 102011009906.9 filed on Jan. 31, 2011, the disclosures of which are incorporated herein by reference.

The invention relates to a dental-implant system having a first implant part provided for being inserted into a jawbone and having a second implant part associated therewith, provided for fixing a dental prosthetic piece, the implant parts being mechanically connectable to each other via a connection pin which is formed onto one of the implant parts and which can be pushed into a receiving channel provided in the other implant part, and the cross-section of the connection pin and the cross-section of the receiving channel associated therewith each presenting in an indexing area a number of main directions in which the radius takes in each case a relative maximum value.

Dental implants can be used in the reconstructive therapy to compensate for the loss of a tooth. They are usually inserted into the jawbone in the place of an extracted or shed tooth, in order to hold there, after a healing-in phase of approximately four to twelve weeks, a prosthetic part serving as a dental prosthesis or a crown. For this purpose, such a dental implant is usually configured as an appropriately shaped metallic body inserted into the jawbone by screwing-in, in the intended place. As a rule, the apical end of the dental implant includes a screw thread, in most cases a self-cutting screw thread, with which the dental implant is inserted into the correspondingly prepared implant bed.

To facilitate the insertion into the patient's mouth and in particular to enable a particularly extensive preparation of the prosthesis properly speaking for its being fixed on the implant already prior to the patient's treatment, for example in a dental laboratory, dental-implant systems can be of a multi-part configuration. In particular, a generally two-part construction can be provided, the dental-implant system comprising a first implant part, also referred to as the actual implant or post part, provided for being inserted into the jawbone, and in addition to this, a second implant part associated therewith, also referred to as mounting-part piece, on which, in turn, the dental prosthetic piece provided as a prosthesis or the like can be mounted. The outer surface of the first implant part or post part is usually provided with a thread, which can be designed as a self-cutting thread or else as a not self-cutting thread. The post part is usually anchored in a correspondingly prepared implant bed of the jawbone. The construction of the thread provided in the external area of the dental implant is usually configured for a high primary stability of the arrangement and a uniform forwarding of the forces arising under the chewing load of the dental implant, into the jawbone.

Usually, a connection pin formed onto one of the implant parts, as a rule the mounting-part piece, is provided for mechanically connecting the implant parts with each other. This pin can be pushed into a receiving channel provided in the other implant part, as a rule the post part. With regard to the choice of geometry and dimensioning, in particular of the cross-sections, the connection pin on the one hand and the receiving channel on the other hand are usually adapted to each other in such a way that mounting is relatively easy and, nevertheless, a good guidance of the components in each other and, thus, a sufficiently high mechanical stability can be achieved. The mounting-part piece, whose upper part is usually fitted with a crown, another prosthetic provision or the like in a manner known as such, can be glued together with the post part via the connection pin pushed into the receiving channel to ensure the mechanical connection. The mounting-part piece can, however, also be pressed into the post part and fixed only via a clamping or else can additionally be fixed by cement or glue.

In view of the forces arising under the chewing load and the desired long service life when using such a dental implant, the mechanical stability of the arrangement under various loads is particularly important. In particular, as a rule, even a rotation or torsion between the mounting-part piece and the post part through external forces, mostly due to the chewing load, shall be counteracted. For this purpose, usually a mechanical indexing in the form of a mechanical lock is used, or the surface pressure between the mounting-part piece and the post part is suitably chosen. In particular, a suitable contouring of the cross-section of the connection pin on the one hand and the receiving channel associated therewith on the other hand can be provided for indexing and to avoid a rotation of the mounting-part piece on the post part, to form the before-mentioned mechanical lock.

However, the mechanical lock between the mounting-part piece and the post part of multi-part implant systems in the manner of an indexing does not only serve the purpose of counteracting a rotational load, but shall in particular also assist the correct insertion of the implant in the patient's mouth with high positional accuracy, keeping the treatment time as short as possible. After the insertion of the implant properly speaking, preferably after the post parts have healed in, the spatial and geometrical data of the remaining teeth (for example antagonist teeth, teeth located mesially and distally of the place of insertion), of the mucosa and of the post part or implant, or of the mounted mounting-part piece have to be considered in such systems in order to manufacture the crown, the bridge or other prostheses. These spatial and geometrical data are needed to manufacture the crown, the bridge or the like with precise fitting and in an anatomically optimized manner.

For this purpose, usually a cast, preferably of silicone or another dental casting material, of the oral situation is made. This cast is preferably filled with gypsum or another dental model material, so that this gypsum model is a duplicate of the patient's oral situation. It gives the dentist and/or the dental technician the information on the position of the remaining teeth, the mucosa, and the inserted post part or implant.

To improve the transmission of position and geometry of the inserted post parts or implants, special casting posts of metal and/or plastic are preferably plugged and/or screwed onto the inserted post parts or implants. Then, the cast in the mouth is produced, preferably with silicone. After the casting material has cured, the casting post either remains on the implant or is taken out with the cast when the latter is removed. When filling the cast, the casting post or mounting post must be placed in the cast and connected with a laboratory implant. This geometrical configuration of the laboratory implant is equal or similar to that of the inserted post part or implant, as far as the connection and the geometry in the direction of the casting post or mounting post is concerned. After filling the cast, with the casting post or mounting post and the laboratory implant being integrated, one gets a gypsum model with cast-in laboratory implant.

If the implant system used possesses an indexing, the latter will have been transferred from the patient's mouth to the gypsum model. The prosthetic provision of the implant(s) is planned and produced on the basis of this gypsum model, the rotational position of the mounting-part piece on the implant playing a decisive role. The above-mentioned indexing of the implant system limits the positioning possibilities of the mounting-part piece on the laboratory implant, so that the correct positioning can be ensured with little expenditure and in a particularly simple manner when placing the mounting-part piece.

The indexing, i.e. the determination of the possible rotational orientation between the mounting-part piece on the one hand and the post part on the other hand is usually achieved by suitably specifying the contour of the cross-sections of the connection pin on the one hand and of the receiving channel on the other hand in the area of their connection. Usually, the cross-sections of the connection pin and, consequently, also of the receiving channel, are configured in a hexagonal shape for that purpose. A hexagonal connection allows six possibilities of positioning the mounting-part piece on the post part. Alternatively, however, designs in the form of Torx or so-called multiple systems with a varying number of elements and varying geometry are also known, the number of positioning possibilities resulting from the rotational symmetry of the cross-section in the connection area between connection pin and receiving channel, whereas in an implant system without indexing, all positions between 0° and 360° can be used.

From DE 10 2008 054 138 A1, an implant system of the above-mentioned type is known which, on the one hand, enables a suitable indexing of the implant in a particularly simple and reliable manner, and with which, on the other hand, a particularly high tightness between mounting-part piece and post part is ensured, even with a low overall height. In this implant system, the cross-section of the connection pin formed onto the mounting-part piece and the cross-section of the receiving channel associated therewith each present a number of main directions in which the radius takes a relative maximum value in each case, the outer contour of the cross-section being chosen such that it has exactly one tangent in each point. The above-mentioned cross-sections are, therefore, chosen, for example, of an oval or elliptic shape.

It is achieved in this way that the radius of the cross-section of the connection pin and, accordingly, of the matching receiving channel in the post part, i.e. the radius or distance of the outer contour of the cross-sectional area from the latter's central point, in particular the center of gravity, referred to a rotation or pivoting around that point, is not constant, but presents maximum values in a number of main directions, i.e. in particular in at least one main direction. When the connection pin is inserted into the receiving channel, these main directions of the connection pin on the one hand and of the receiving channel on the other hand are brought to overlap, so that the desired orientation of the mounting-part piece fixed on the connection pin relative to the post part is obtained.

The invention is based on the task to develop a dental implant of the above-mentioned type in such a manner that it offers a still further increased mechanical load-carrying ability and thus a particularly long service life when used in the patient's mouth.

This task is solved according to the invention in that the radius of the outer cross-section of the implant part including the receiving channel, viewed in the longitudinal direction of said implant part, at least in a partial area, preferably in the indexing area, i.e. in the area where the implant system is provided with an indexing, also takes a relative maximum value whichin a tolerance range of each of the main directions.

Each maximum value of the radius as a function of the rotational angle around the central point or center of gravity of the cross-sectional area can be—in the same way as in the case of the cross-section of the receiving channel or of the connection pin—the absolute maximum value of the radius or else a local or relative maximum value of the radius, at which the radius takes a higher value in the respective main direction than in immediately adjacent orientations.

The invention starts out on the consideration that the configuration of the receiving channel with a non-round cross-section presenting a number of local maxima of the radius in the respective implant part will as a rule entail a varying wall thickness in the post part, viewed in the direction of rotation about the latter's longitudinal axis, if the post part—as is generally usual—is designed with a round outer cross-section. In particular in the direction of the main directions defined by the maximum values of the radius in the cross-section of the receiving channel, the wall thickness of the implant part including the receiving channel will in this case present minima, which correspond to mechanical weakening zones. These weakening zones might be detrimental in particular to the fatigue properties of the implant system, because they may undesirably promote, for example, the formation of microcracks or the like. This could be counteracted by a correspondingly large wall thickness of the implant part concerned, which would, however, lead to undesirably large outer diameters of the respective implant part, depending on design and degree of requirements.

In order to avoid this and to guarantee, nevertheless, a particularly high mechanical strength and, thus, a permanent load-carrying ability of the implant system, the outer cross-section of the implant part including the receiving channel should be configured in the manner of a contouring adapted to the receiving channel. It is provided for this purpose that the outer cross-section of the respective implant part also presents local maxima, at least in the connection area with the connection pin, viewed in the direction of rotation about the latter's longitudinal axis, in those areas where the cross-section of the receiving channel, too, forms the local maxima (and thus, the before-mentioned main directions).

Advantageous embodiments of the invention are the subject matter of the dependent claims.

Advantageously, in particular the contour of the outer cross-section of the respective implant part is adapted with relatively high precision to the cross-section of the receiving channel. To guarantee this, the tolerance range for the orientation of the respective main directions, i.e. the main directions of the outer cross-section of the respective implant part on the one hand and the main directions of the cross-section of the receiving channel on the other hand, is preferably approximately 20°, more preferably approximately 10°, particularly preferably approximately 4°. In other words: preferably, the respective main direction of the outer cross-section of the respective implant part coincides in a range of +−10°, more preferably of +−5°, particularly preferably of +−2°, with the respective main direction associated therewith of the cross-section of the receiving channel.

In another advantageous embodiment, the number of relative maximum values of the radius of the outer cross-section of the implant part including the receiving channel is equal to the number or to an integer multiple of the number of main directions.

In order to enable a particularly slim overall construction of the respective components, in particular of the post part, and to particularly promote in this way the process of healing-in and integration into the bone, the post part is in a particularly advantageous embodiment configured in such a way that—with the outer diameter of the respective implant part including the receiving channel being in principle as small as possible—its wall thickness presents in the indexing area, viewed over the periphery, a variation of maximally 20%, preferably of maximally 10%, particularly preferably of maximally 5%. The adaptation of the contourings of the cross-section of the receiving channel on the one hand and the outer cross-section of the implant part on the other hand to each other is, therefore, preferably chosen to a great extent in such a manner that a weakening of the wall thickness and, thus, a reduction of the mechanical load-carrying ability in these areas is kept accordingly low. In this way, it is possible in a particularly reliable manner, even with the slim overall construction of the parts—desired as such—to safeguard a mechanical strength which is considered as sufficient.

Viewed in the longitudinal direction of the connection pin or the receiving channel, these two can be configured with constant cross-sections. Advantageously, however, the cross-sections taper towards the free end of the connection pin, in a particularly advantageous embodiment, in a conical design, so that a good frictional connection with high tightness can be achieved in a particularly simple manner.

In order to ensure in the present system, in which the orientation or indexing of the mounting-part piece relative to the post part is effected on the basis of the contour, also the usually desired high tightness in the area of mechanical contact between the mounting-part piece and the post part, i.e. in particular between the connection pin and the inner surface of the receiving channel, in a particularly reliable manner, it is provided in another advantageous embodiment to suitably choose the outer contour of the cross-sectional area of the connection pin and accordingly, of the receiving channel also between the above-mentioned main directions. For this purpose, the outer contour is advantageously designed substantially without corners, so that the outer contour of the cross-section has exactly one tangent in each point.

Furthermore, a particularly high tightness can be achieved by designing the outer contour in a bulged or outwardly curved or domed shape in the segments between the main directions. This embodiment leads to the fact that defects of shape, i.e., for example, local contour deviations on account of production or the like, between the cross-sections due to warpings and local deformations resulting therefrom are compensated and the cross-sections are adjusted to each other, when the connection pin is inserted into the receiving channel. The outwardly curved or bulged embodiment of the contour segments has a result analogous to a criterion of a surface oval, namely that any straight line intersects the respective cross-sectional area in maximally two points.

In an advantageous embodiment, the outer contour of the cross-section is in addition chosen such that in the areas between each two main directions, it corresponds to an oval segment. In other words: advantageously, the outer contour additionally fulfills in the segments between each two main directions the second criterion of a surface oval, namely that exactly one tangent exists for each point of the contour segment. In this way, the outer contour follows in the respective segment a relatively smooth course without forming any corners.

In a particularly advantageous development, the dental implant is additionally designed such that the connection pin formed onto the mounting-part piece or onto the respective implant part and the receiving channel associated thereto in the post part or in the respective other implant part are each configured under complete avoidance of any corners in the cross-sectional contour. Thus, the respective cross-section advantageously fulfills also in the points of the outer contour in the respective main directions the second criterion of a surface oval, namely that for these points, too, exactly one tangent exists, thus forming, in its entirety, an oval. Thus, the outer contour follows a rounded course also in the respective main directions. It is precisely this relatively round course, given also in the main directions, which ensures that any slight misorientations are automatically corrected in the manner of a guided self-centering without obstructions, jams or catchings, when the connection pin is inserted into the receiving channel.

The advantages achieved with the invention consist in particular in that a reliable indexing is possible without excessively weakening the respective implant part, in particular the post part, from the point of view of material, due to the adaptation of the cross-sectional contours of the receiving channel on the one hand and of the outer cross-section of the respective implant part on the other hand, effected in the connection area between connection pin and receiving channel, even with a slim overall configuration, especially of the post part, which favors the healing-in process. Consequently, the post part can be configured with a correspondingly high mechanical strength and load-carrying ability. This favors in particular the fatigue properties of the system, because the above-mentioned weakening zones might to a particularly great extent lead to a formation of microcracks or the like, under the permanent load usual in case of use in the patient's mouth.

For the case that the receiving channel is worked into the post part and the latter is consequently provided with a non-round, correspondingly adapted outer cross-section, the post part can also be provided with an external thread provided for anchoring in the patient's mouth. The post part will then have—in corresponding adaptation to the receiving channel—a thread core with a non-round cross-section—corresponding to the before-mentioned outer cross-section of the post part—, whereby, however, the outer cross-section, for its part, of the thread surrounding the thread core can be provided with a round outer cross-section to facilitate its mounting in the patient's mouth.

An exemplary embodiment of the invention is explained in detail by means of a drawing, in which.

Identical parts are marked with the same reference numbers in all figures.

Figure 1:
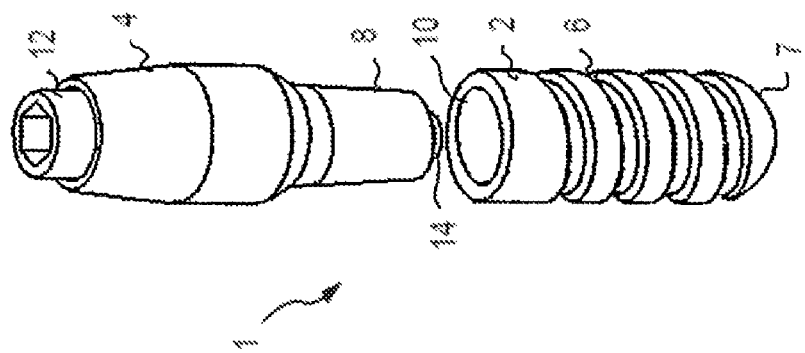
FIG. 1 is a partly sectional view of a dental implant.
Figure 2:
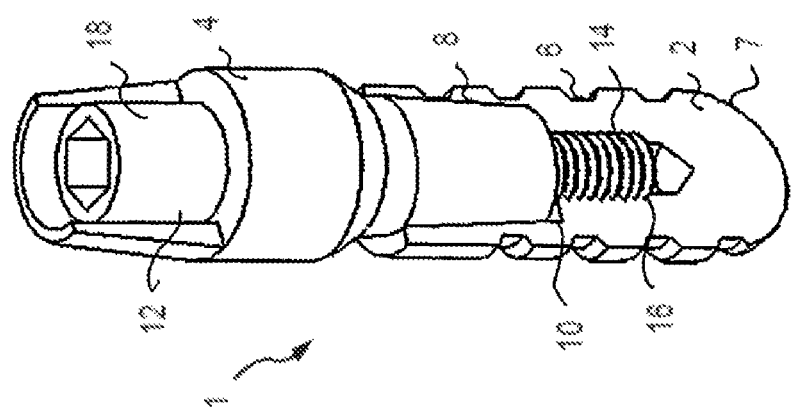
FIG. 2 is an exploded view of the dental implant of FIG. 1.

The dental implant 1 or dental-implant system shown in a partly sectional view in FIG. 1 in mounted state and in an exploded view in FIG. 2 is provided for use in the jawbone in the place of an extracted or shed tooth, in order to hold there a prosthetic part serving as a dental prosthesis or a crown. For this purpose, the dental implant 1 is of a multi-part configuration and comprises a first implant part 2 configured as a so-called post part and a second implant part 4 associated therewith, also referred to as mounting-part piece, provided for fixing a dental prosthetic piece.

The first implant part 2 or post part is provided on its outside with an external thread 6, which is configured, in particular at its apical end 7, as a self-cutting screw thread, with which the first implant part 2 or post part can be inserted into the jawbone by screwing in, in the intended place. The pitch of the thread 6 can be uniform or else variable, it being possible to also take into consideration, through a suitable choice of parameters, any different biological conditions or the like, as well as different growing-in behaviors. Construction and configuration of the thread 6 are designed in particular in view of a desired high primary stability and a uniform forwarding of the forces arising under the chewing load of the dental implant 1, into the jawbone.

In order to enable an insertion into the post part or first implant part 2 with high mechanical stability, after having suitably fixed the dental prosthetic piece or the prosthesis on the mounting-part piece or second implant part 4, a connection pin 8 is formed onto the second implant part 4, which can be pushed into a receiving channel 10 associated therewith, provided in the first implant part 2. By pushing the connection pin 8 into the receiving channel 10, the implant parts 2, 4 are mechanically connected with each other. The mechanical connection of the post part 2 and the mounting-part piece 4 is effected via an associated connection screw 12, whose external thread 14 is screwed into an internal thread 16 provided in the post part 2, whereby the screw head 18 of the connection screw 12 presses the mounting-part piece 4 onto the post part 2.

The dental implant 1 is specifically designed for ensuring, after a suitable preparation of the mounting-part piece 4, a reliable and mechanically stable rotational orientation of the mounting-part piece 4 even when relatively high forces arise, in particular through the chewing load. It should in particular also be possible to insert and integrate the mounting-part piece 4 provided with the dental prosthetic piece into the post part 2 grown into the jawbone, in a relatively short treatment time. For this purpose, the outer contour of the connection pin 8 matches the inner contour of the receiving channel 10, it being possible that both of them are of conical shape, viewed in the longitudinal direction.

Figure 4:
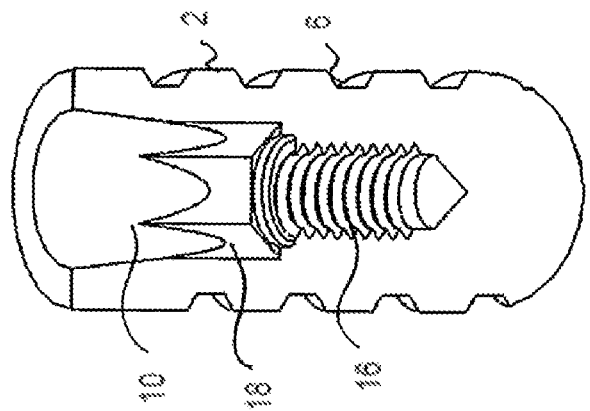
FIG. 4 is a sectional view of an alternative post part, and FIGS. 5 to 9 each show the cross-section of the indexing area of the dental-implant system of FIG. 1.
Figure 3:
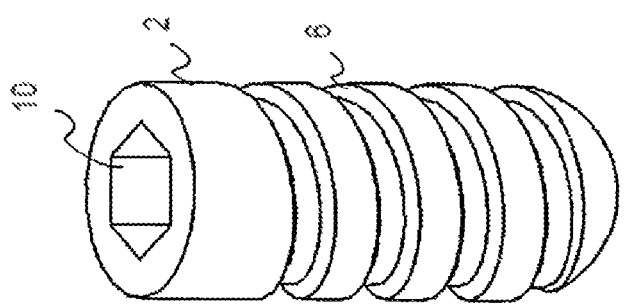
FIG. 3 shows a post part for being used in the dental implant of FIG. 1.
Figure 6:
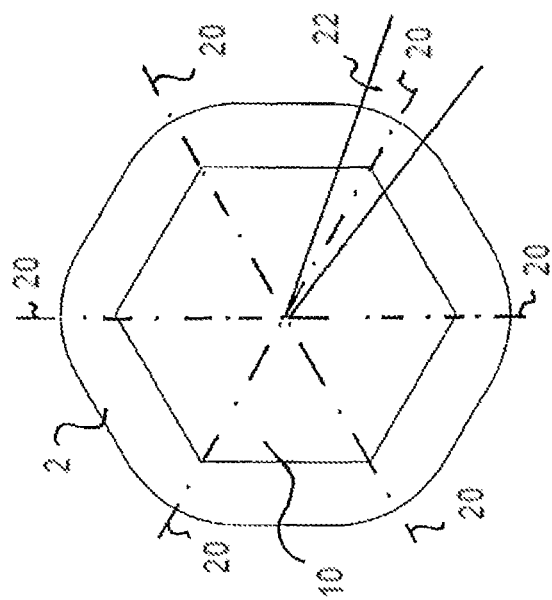

The outer contour of the connection pin 8—and the correspondingly adapted inner contour of the receiving channel 10—are as such configured in the exemplary embodiment with a cross-section with a multiple symmetry, so that a rotational locking mechanism is created when the above-mentioned components are joined and thus, a reliable rotational orientation of the mounting-part piece 4 relative to the post part 2 can be set. As an example thereof, FIG. 3 shows the first implant part 2 or post part with a receiving channel 10, which, in the manner of a hexagonal configuration, has a sextuple symmetry. As an alternative exemplary embodiment, FIG. 4 is a sectional view of a post part or first implant part 2, in which, for the purpose of an indexing or for creating a rotational locking mechanism, an additional indexing element is arranged on the end side of the connection pin 8, which indexing element, for its part, has a cross-section with a multiple symmetry and, in mounted state, engages into a corresponding associated channel end piece 18 in the receiving channel 10.

That means that in both variants of the dental implant 1, the cross-section of the connection pin 8 formed onto the mounting-part piece 4 and, accordingly, the cross-section of the receiving channel 10 associated therewith, as can be seen in the cross-sectional views of FIGS. 4 to 9, each present in the indexing area a number of main directions 20 in which the radius takes in each case a relative maximum value. The before-mentioned cross-sections are, therefore, for example oval or elliptic or, as shown, in particular hexagonal.

In this way, it is achieved that the radius of the cross-section of the connection pin 8 and, accordingly, of the receiving channel 10 adapted thereto in the post part 2, i.e. the radius or distance of the outer contour of the cross-sectional area from the latter's central point, in particular the center of gravity, related to a rotation or pivoting around that center of gravity, is not constant, but takes maximum values in the main directions 20. When the connection pin 8 is inserted into the receiving channel 10, these main directions 20 are brought to overlap by the connection pin 8 on the one hand and the receiving channel 10 an the other hand, so that the desired orientation of the mounting-part piece 4 fixed on the connection pin 8 relative to the post part 2 is obtained.

Figure 5:
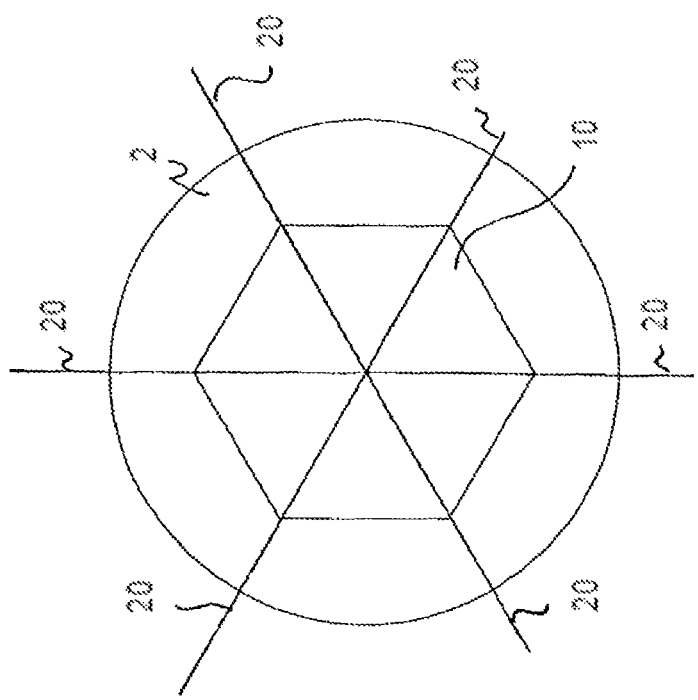

In general, the outer cross-section of the post part or first implant part 2 is of round shape, as can be seen in the representation for a known implant system in FIG. 5. Therefore, relatively thin-walled areas with little wall thickness are formed in the areas of the main directions 20. These weakening zones might, therefore, in particular under permanent load, promote the formation of microcracks or the like in the material body, which might finally lead to ruptures of the material.

By contrast, the dental implant 1 is purposefully designed such that it possesses a particularly high mechanical load-bearing ability and thus, a particularly long service life when used in the patient's mouth. In order to purposefully avoid at the same time mechanical weak points through too small wall thicknesses, even with a relatively slim construction of the components, the outer cross-section of the post part 2 is adapted, at least in the indexing area, to the before-mentioned cross-section of the receiving channel 10. As can be seen in particular in the cross-sectional representation of FIG. 6, the radius of the outer cross-section of the implant part 2 including the receiving channel 10 also takes a relative maximum value in the indexing area within a tolerance range 22 of each of the main directions 20. In the exemplary embodiment, a tolerance range of approximately 4° is predefined, i.e. within an admissible deviation of approximately +−2°, the maximum values of the radius of the outer cross-section of the implant part 2 including the receiving channel 10 lie in the direction of the respective main direction 20 (so-called "in-phase orientation").

Figure 8:
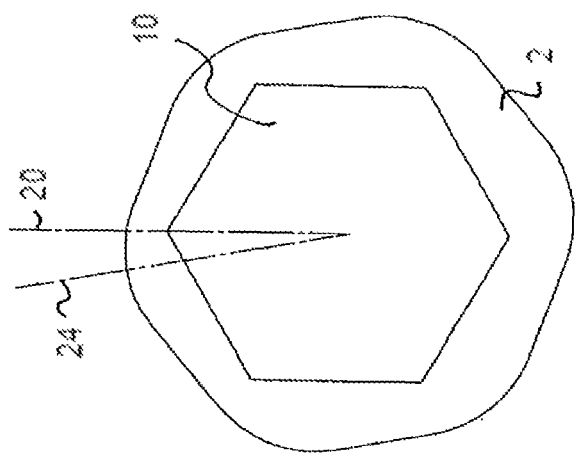
Figure 7:
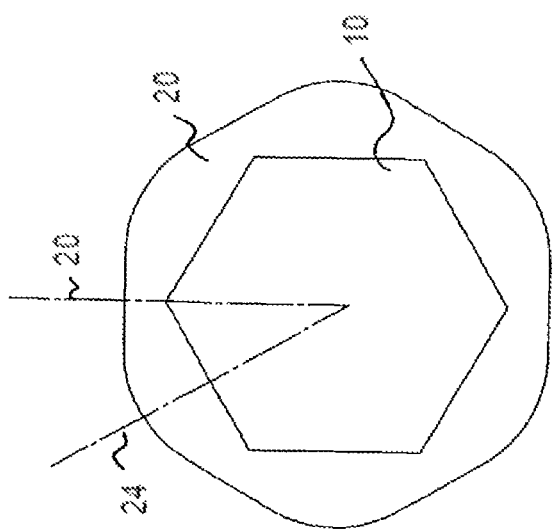

An example for an unfavorable orientation in the present sense is shown, by contrast, in FIG. 7, in which the direction of the maximum value of the radius of the outer diameter of the post part 2, indicated by the line 24, deviates from the main direction 20 by more than the desired 10°. By way of comparison, FIG. 8 shows an example, in which the directional deviation between the line 24 and the main direction 20 amounts to approximately 10° and can, therefore, be considered as acceptable in the present sense.

Figure 9:
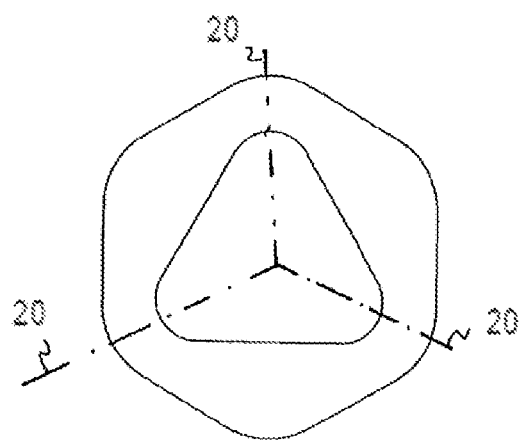

Furthermore, the number of relative maximum values of the radius of the outer cross-section of the implant part 2 including the receiving channel 10 is in the examples shown equal to the number or to an integer multiple of the number of main directions 20. An example of the latter variant is represented in FIG. 9, in which six maxima are provided in the outer contour of the post part 2 for three main directions 20.

To ensure a mechanical stability of the dental-implant system 1 which can be considered as sufficient, the latter is, furthermore, configured such that the wall thickness of the implant part 2 including the receiving channel 10 presents in the indexing area, viewed over the periphery, a variation of maximally 20%, preferably of maximally 10%, particularly preferably of maximally 5%.

Furthermore, in the dental implant 1, the outer contour of the cross-section of the connection pin 8 and, accordingly, of the receiving channel 10, is chosen such that it is intersected by any straight line in maximally two points. In this way, a particularly high tightness can be achieved when mounting the system, because the outer contour of the cross-section is designed in a bulged or outwardly curved or domed shape in the segments between the main directions 20. This embodiment leads to the fact that defects of shape, i.e., for example, local contour deviations on account of production or the like, between the cross-sections due to warpings and local deformations resulting therefrom are compensated and the cross-sections are adjusted to each other, when the connection pin 8 is inserted into the receiving channel 10. The outwardly curved or bulged embodiment of the contour segments has a result analogous to a criterion of a surface oval, namely that any straight line intersects the respective cross-sectional area in maximally two points.

LIST OF REFERENCE NUMBERS

1 Dental-implant system
2 Implant part
4 Implant part
6 External thread
7 Apical end
8 Connection pin
10 Receiving channel
12 Connection screw
14 External thread
16 Internal thread
18 Channel end piece
20 Main direction
22 Tolerance range

The invention claimed is:

1. A dental-implant system, comprising:
a first implant part provided for being inserted into a jawbone, the first implant part having an external thread on an outer surface of the first implant part, and the first implant part having an outer cross-section and a receiving channel with a cross-section, and in an indexing range the outer cross-section has a plurality of main directions in which a radius has a relative maximum value and thus a higher value than in directly adjacent rotational orientations;
a second implant part provided for fixing a dental prosthetic piece, the second implant part having a connection pin that is mechanically connectable to the receiving channel provided in the first implant part;
wherein in the indexing range the cross-section of the receiving channel has a plurality of main directions in which a radius has a relative maximum value and thus a higher value than in directly adjacent rotational orientations;
wherein at least one main direction of the outer cross-section and at least one main direction of the cross-section of the receiving channel in the indexing range are oriented within a tolerance range of each other with respect to longitudinal axis of the first implant part, wherein the tolerance range is approximately +−10° with respect to the longitudinal axis of the first implant part; and
wherein the main directions of the outer cross-section and the receiving channel are equally spaced about the longitudinal axis of the first implant part.

2. The dental-implant system of claim 1, wherein the tolerance range is approximately +−5° with respect to the longitudinal axis of the first implant part.

3. The dental-implant system of claim 2, wherein a wall thickness of the first implant part presents in the area of the maximum values of the cross-section radius of the receiving channel, viewed over the periphery, a variation of maximally 20%.

4. The dental-implant system of claim 2, wherein the cross-section of the connection pin tapers towards a free end of the connection pin.

5. The dental-implant system of claim 2, wherein an outer contour of the cross-section of the receiving channel is chosen such that it is intersected by any straight line in maximally two points.

6. The dental-implant system of claim 1, wherein the number of main directions of the outer cross-section of the first implant part is an integer multiple of the number of main directions of the cross-section of the receiving channel.

7. The dental-implant system of claim 6, wherein the cross-section of the connection pin tapers towards a free end of the connection pin.

8. The dental-implant system of claim 6, wherein an outer contour of the cross-section of the receiving channel is chosen such that it is intersected by any straight line in maximally two points.

9. The dental-implant system of claim 1, wherein a wall thickness of the first implant part presents in the area of the maximum values of the cross-section radius of the receiving channel, viewed over the periphery, a variation of maximally 20%.

10. The dental-implant system of claim 9, wherein the wall thickness of the first implant part presents in the area of the maximum values of the cross-section radius of the receiving channel, viewed over the periphery, a variation of maximally 10%.

11. The dental-implant system of claim 10, wherein the wall thickness of the first implant part presents in the area of the maximum values of the cross-section radius of the receiving channel, viewed over the periphery, a variation of maximally 5%.

12. The dental-implant system of claim 1, wherein the cross-section of the connection pin tapers towards a free end of the connection pin.

13. The dental-implant system of claim 1, wherein an outer contour of the cross-section of the receiving channel is chosen such that it is intersected by any straight line in maximally two points.

14. The dental-implant system of claim 1, wherein the outer cross-section of the first implant part comprises a plurality of flat edges joined together with curved edges at the relative maximum values of the outer cross-section; and
wherein the cross-section of the receiving channel comprises a plurality of flat edges joined together with vertices at the relative maximum values of the receiving channel.

15. The dental-implant system of claim 14, wherein the outer cross-section of the first implant part is substantially hexagonally shaped.

16. A dental-implant system, comprising:
a first implant part having an external thread configured to anchor the first implant part in a jawbone, the first implant part including:
an outer cross-section having a plurality of main directions in an indexing range of the first implant part, the plurality of main directions of the outer cross-section marking maximum distances of the outer cross-section from a longitudinal axis of the first implant part;
an inner cross-section defining a receiving channel of the first implant part, the inner cross-section having a plurality of main directions in the indexing range of the first implant part, the plurality of main directions of the inner cross-section marking maximum distances of the inner cross-section from the longitudinal axis of the first implant part;

wherein at least one main direction of the outer cross-section and at least one main direction of the inner cross-section substantially overlap within a tolerance range, where the tolerance range is approximately +−10° with respect to the longitudinal axis of the first implant part;

wherein the main directions of the outer cross-section and the inner cross-section are equally spaced about the longitudinal axis of the first implant part;

a second implant part having a connection pin that is mechanically connectable to the receiving channel of the first implant part.

17. The dental-implant system of claim 16, wherein the outer cross-section of the first implant part comprises a plurality of flat edges joined together with curved edges at the maximum distances of the outer cross-section; and wherein the inner cross-section of the first implant part comprises a plurality of flat edges joined together with vertices at the maximum distances of the inner cross-section.

18. The dental-implant system of claim 16, wherein the tolerance range is approximately +−5° with respect to the longitudinal axis of the first implant part.

19. The dental-implant system of claim 16, wherein the number of main directions of the outer cross-section of the first implant part is an integer multiple of the number of main directions of the inner cross-section of the first implant part.

20. The dental-implant system of claim 16, wherein the outer cross-section of the first implant is substantially hexagonally shaped.

* * * * *